United States Patent
Aliprandi et al.

(10) Patent No.: US 12,430,752 B2
(45) Date of Patent: Sep. 30, 2025

(54) TRAINING PROCEDURE AND SYSTEM FOR ARTIFICIAL INTELLIGENCE INTENDED FOR THE ANALYSIS OF MAMMOGRAPHIC DATA FOR THE IDENTIFICATION OR EXCLUSION OF THE PRESENCE OF BREAST CANCER

(71) Applicant: Aigea Medical S.R.L., Pisa (IT)

(72) Inventors: Carlo Aliprandi, Pisa (IT); Michele Cafagna, Barletta (IT); Lorenzo De Mattei, Pisa (IT); Andrea Tesei, Latina (IT)

(73) Assignee: AIGEA MEDICAL S.R.L., Pisa (IT)

( * ) Notice: Subject to any disclaimer, the term of this patent is extended or adjusted under 35 U.S.C. 154(b) by 820 days.

(21) Appl. No.: 17/582,180

(22) Filed: Jan. 24, 2022

(65) Prior Publication Data
US 2022/0237776 A1    Jul. 28, 2022

(30) Foreign Application Priority Data
Jan. 25, 2021   (IT) .................. 102021000001244

(51) Int. Cl.
*G06T 7/00* (2017.01)
*A61B 6/00* (2006.01)
(Continued)

(52) U.S. Cl.
CPC ............ *G06T 7/0012* (2013.01); *A61B 6/502* (2013.01); *A61B 6/5217* (2013.01);
(Continued)

(58) Field of Classification Search
CPC ......... G06T 7/0012; G06T 2207/10081; G06T 2207/10088; G06T 2207/10112;
(Continued)

(56) References Cited

U.S. PATENT DOCUMENTS 9,129,362 B2    9/2015  Jerebko
2017/0071562 A1  3/2017  Suzuki
(Continued)

FOREIGN PATENT DOCUMENTS

WO    2019060843 A1    3/2019
WO    2019239153 A1    12/2019

OTHER PUBLICATIONS

Italian Search Report mailed Sep. 15, 2021 for IT 102021000001244 to Algea Medical S.R.L. filed Jan. 25, 2021.
(Continued)

*Primary Examiner* — Kent Yip
(74) *Attorney, Agent, or Firm* — Vorys, Sater, Seymour and Pease LLP

(57) ABSTRACT

Training procedure for artificial intelligence for mammographic data analysis for breast cancer detection including acquiring mammographic data from a plurality of sources and including mammographic images, report texts relating to images, and structured data obtained from SIO, EMR, BI-RADS and MOM including at least metadata relating to part of the images, processing mammographic data through algorithms implementing a multimodal deep neural network (DNN) developing a mammographic data analysis model by performing learning based on sub-phases of first multi-label classification of each image implemented through a model with Encoder-Decoder architecture based on convolutional neural network (CNN) and/or Transformers, association of parts of report texts with images and/or parts of structured data, implemented through a model with Encoder-Decoder architecture based on a bidirectional long-term memory (Bi-LSTM) and/or Transformers, second multi-label classification of mammographic structured data implemented through a model with Encoder-Decoder architecture based on CNN and/or Transformers.

14 Claims, 1 Drawing Sheet

(51) Int. Cl.
| | |
|---|---|
| *A61B 6/50* | (2024.01) |
| *A61B 8/00* | (2006.01) |
| *G06N 3/04* | (2023.01) |
| *G06V 10/764* | (2022.01) |
| *G06V 10/774* | (2022.01) |
| *G06V 10/82* | (2022.01) |
| *G16H 10/60* | (2018.01) |
| *G16H 15/00* | (2018.01) |
| *G16H 30/20* | (2018.01) |
| *G16H 30/40* | (2018.01) |

(52) U.S. Cl.
CPC ............. *A61B 8/5223* (2013.01); *G06N 3/04* (2013.01); *G06V 10/764* (2022.01); *G06V 10/774* (2022.01); *G06V 10/82* (2022.01); *G16H 10/60* (2018.01); *G16H 15/00* (2018.01); *G16H 30/20* (2018.01); *G16H 30/40* (2018.01); *G06T 2207/10081* (2013.01); *G06T 2207/10088* (2013.01); *G06T 2207/10112* (2013.01); *G06T 2207/20081* (2013.01); *G06T 2207/20084* (2013.01); *G06T 2207/30068* (2013.01); *G06T 2207/30096* (2013.01); *G06V 2201/03* (2022.01); *G06V 2201/10* (2022.01)

(58) Field of Classification Search
CPC . G06T 2207/20081; G06T 2207/20084; G06T 2207/30068; G06T 2207/30096; A61B 6/502; A61B 6/5217; A61B 8/5223; G06V 10/764; G06V 10/82; G06V 2201/03; G06V 2201/10; G16H 10/60; G16H 15/00; G16H 30/20; G16H 30/40
See application file for complete search history.

(56) References Cited

U.S. PATENT DOCUMENTS

2020/0321130 A1\* 10/2020 Ha .................... G16H 50/30
2022/0020151 A1\* 1/2022 Sainz de Cea ....... G06T 7/0016

OTHER PUBLICATIONS

Lee Hyebin et al: "Building a Breast—Sentence Dataset: Its Usefulness for Computer-Aided Diagnosis", 2019 IEEE/CVF International Conference On Computer Vision Workshop (ICCVW), IEEE, Oct. 27, 2019, pp. 440-449, XP033732548.

Yan Rui et al: "Integration of Multimodal Data for Breast Cancer Classification Using a Hybrid Deep Learning Method", Jul. 24, 2019, Advances in Databases and Information Systems; [Lecture Notes in Computer Science; Lect. Notes Computer], Springer International Publishing, Cham, pp. 460-469, XP047515356.

Liu Yi et al: "Breast Cancer Medical Image Analysis Based on Transfer Learning Model", Jul. 6, 2018, ICIAP: International Conference On Image Analysis and Processing, 17th International Conference, 17th International Conference, Naples, Italy, Sep. 9-13, 2013. Proceedings; [Lecture Notes in Computer Science; Lect. Notes Computer], Springer, Berlin, Heidelberg, pp. 44-53, XP047481928.

\* cited by examiner

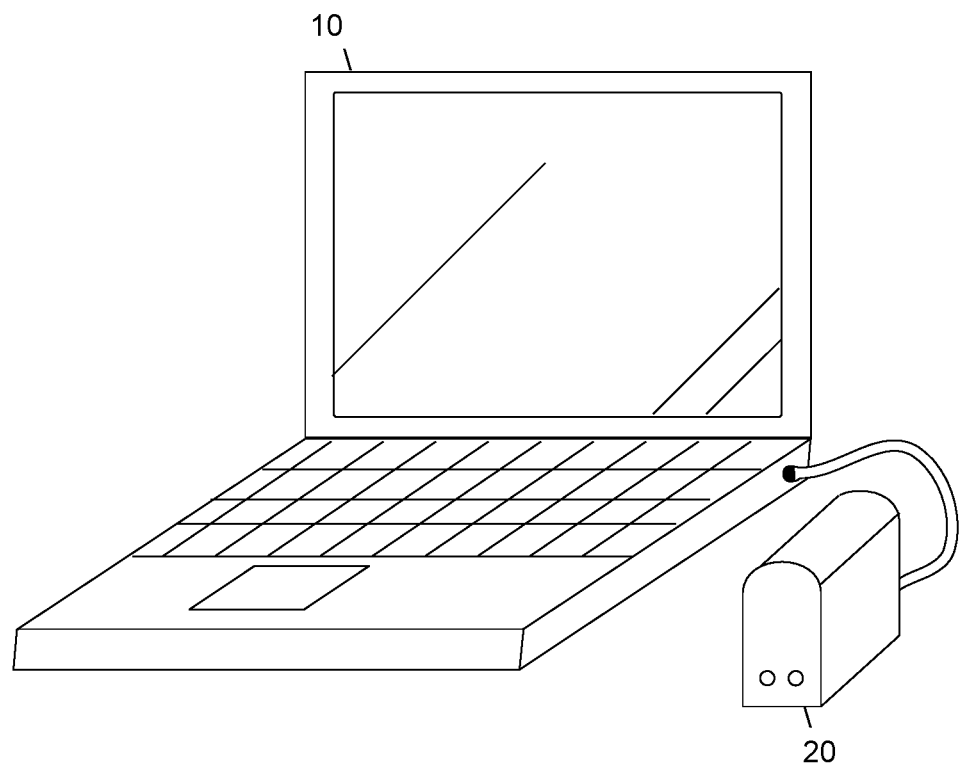

TRAINING PROCEDURE AND SYSTEM FOR ARTIFICIAL INTELLIGENCE INTENDED FOR THE ANALYSIS OF MAMMOGRAPHIC DATA FOR THE IDENTIFICATION OR EXCLUSION OF THE PRESENCE OF BREAST CANCER

FIELD OF THE INVENTION

The present invention relates to a training procedure and system for artificial intelligence intended for the analysis of mammographic data for the identification or exclusion of the presence of breast cancer of the type specified in the preamble of the first claim.

In particular, the present invention relates to a process and relative training system of an artificial intelligence to support competent personnel, for example radiologists, breast specialists and oncologists, for the analysis of mammographic data including at least mammographic radiographs and early diagnosis. breast cancer, by identifying true negative and true positive cases.

BACKGROUND OF THE INVENTION

Similar procedures and systems are described in the documents "Building a Breast-Sentence Dataset: Its Usefulness for Computer-Aided Diagnosis", LEE HYEBIN ET AL, 2019 IEEE/CVF INTERNATIONAL CONFERENCE ON COMPUTER VISION WORKSHOP (ICCVW), IEEE, 27 Oct. 2019 (2019-10-27), pages 440-449, XP033732548, DOI: 10.1109/ICCVW.2019.00056; "Integration of Multimodal Data for Breast Cancer Classification Using a Hybrid Deep Learning Method", YAN RUI ET AL, 24 Jul. 2019 (2019-07-24), ADVANCES IN DATABASES AND INFORMATION SYSTEMS; [LECTURE NOTES IN COMPUTER SCIENCE; LECT.NOTES COMPUTER], SPRINGER INTERNATIONAL PUBLISHING, CHAM, PAGE (S) 460-469, XP047515356, ISBN: 978-3-319-10403-4; "Breast Cancer Medical Image Analysis Based on Transfer Learning Model", 6 Jul. 2018 (2018-07-06), ICIAP: INTERNATIONAL CONFERENCE ON IMAGE ANALYSIS AND PROCESSING, 17TH INTERNATIONAL CONFERENCE, NAPLES, ITALY, Sep. 9-13, 2013. PROCEEDINGS; [LECTURE NOTES IN COMPUTER SCIENCE; LECT.NOTES COMPUTER], SPRINGER, BERLIN, HEIDELBERG, PAGE (S) 44-53, XP047481928, ISBN: 978-3-642-17318-9; and "Robust breast cancer detection in mammography and digital breast tomosynthesis using an annotation-efficient deep learning approach", LOTTER WILLIAM ET AL, NATURE MEDICINE, vol. 27, no. 2, pages 244-249, XP037370416, ISSN: 1078-8956, DOI: 10.1038/541591-020-01174-9.

As is known, the breast cancer is the most common type of cancer among women, accounting for 25% of all cancers. Unfortunately, one in eight women is also generally affected by breast cancer throughout their life.

In this context, prevention was the only available option and early detection of cancer symptoms proved crucial.

In this sense, the development of diagnostic systems based on digital imaging is considered fundamental and mammography screening has therefore become a practical practice, suggested and supported extensively in the Health Services, as it falls within the Essential Levels of Assistance (LEA).

For example, in Italy, approximately four million women, corresponding to 7% of the population, undergo mammography screening every year.

In order to improve the identification of possible breast cancers and to support the diagnosis work of the expert staff, various different analysis systems have been developed over the years.

Patent application WO2019239153 describes a method and relative system for the analysis of medical images comprising the steps of receiving the image, analysis aimed at its characterization and generation of an indicative output of one or more medical treatments and tests, in which such additional medical tests can be computed tomography (CT), ultrasound, MRI, Scan Tomosynthesis and biopsy and in which the images can be mammograms or X-rays and in which the analytical step is carried out by a Machine Learning model based on a convolutional neural network (CNN). In summary, the document claims the use of medical images such as X-rays and mammograms, which also include, albeit in a very general way, 3D digital mammograms such as DBT.

The patent application WO2019/060843 from the company NVIEW MEDICAL which claims the priorities US201762562165P of 2017-09-22 and US201862624663P 2018-01-31, is an imaging system that includes generation of an image data set, processing and reconstruction breast cancer image of the target by machine learning, and in which the imaging technique is alternatively: computer tomography (CT), Cone Beam CT, tomosynthesis or an ultrasound imaging system.

The ALARA SYSTEMS patent US2017071562 describes a method and related system for converting low dose X-ray 3D tomosynthesis images into high dose tomosynthesis images through machine learning processes. The patent granted under number U.S. Pat. No. 9,129,362 from Siemens Healthcare claims a method and system for receiving and processing breast cancer analysis using machine learning, in which such images are obtained through Digital Breast Tomosynthesis (DBT).

The known technique described includes some important drawbacks.

In particular, the known systems and methods are mainly, if not entirely, based on images. Therefore, such systems require very substantial training data, consisting of a very large number of images, which are difficult to find.

Indeed, it is known that the acquisition of high quality, interoperable and anonymous health images from health institutions is usually costly in terms of time and resources due to legal, technical and workflow barriers. The legal barrier arises due to the strict regulation of patient data protection and privacy. The technical barrier arises due to the storage and access of patient data across many different clinical systems that are not interoperable. The workflow barrier arises because legal and technical barriers often result in manual processes that prevent automated workflows, such as for anonymization, image extraction or reports. In this sense, several works have shown that it takes 5-9 human years to anonymize and manually tag the 300,000-500,000 training images that artificial intelligence algorithms typically require to achieve precision comparable to that of a radiologist.

SUMMARY OF THE INVENTION

In this situation, the technical task underlying the present invention is to devise a new training procedure and system for artificial intelligence intended for the analysis of multimodal mammographic data (reports, structured data and digital images) for the identification or exclusion of the presence of cancer capable of substantially obviating at least part of the aforementioned drawbacks.

Within the scope of said technical task, it is an important aim of the invention to obtain a procedure and the relative system that allow to realize an artificial intelligence capable of helping the diagnosis work of qualified personnel, for example a radiologist or a breast specialist, by providing tools of very accurate mammography data analysis.

Another important object of the invention is to realize a training procedure and system for artificial intelligence intended for the analysis of mammographic data for the identification or exclusion of the presence of breast cancer which is easily achievable and allows to obtain good performance values even at in the face of limited amounts of data.

The technical task and the specified aims are achieved by a mammographic data analysis procedure and system for the identification or exclusion of the presence of breast cancer as claimed in the annexed claim 1.

Preferred technical solutions are highlighted in the dependent claims.

In the present document, the measurements, values, shapes and geometric references (such as perpendicularity and parallelism), when associated with words like "about" or other similar terms such as "approximately" or "substantially", are to be considered as except for measurement errors or inaccuracies due to production and/or manufacturing errors, and, above all, except for a slight divergence from the value, measurements, shape, or geometric reference with which it is associated. For instance, these terms, if associated with a value, preferably indicate a divergence of not more than 10% of the value.

Moreover, when used, terms such as "first", "second", "higher", "lower", "main" and "secondary" do not necessarily identify an order, a priority of relationship or a relative position, but can simply be used to clearly distinguish between their different components.

Unless otherwise specified, as results in the following discussions, terms such as "treatment", "computing", "determination", "calculation", or similar, refer to the action and/or processes of a computer or similar electronic calculation device that manipulates and/or transforms data represented as physical, such as electronic quantities of registers of a computer system and/or memories in, other data similarly represented as physical quantities within computer systems, registers or other storage, transmission or information displaying devices.

The measurements and data reported in this text are to be considered, unless otherwise indicated, as performed in the International Standard Atmosphere ICAO (ISO 2533:1975).

BRIEF DESCRIPTION OF THE DRAWING

FIG. 1 shows a drawing of a computer connected to an external hard disk for an embodiment of a data processing system of the invention.

DETAILED DESCRIPTION OF THE INVENTION

The training procedure for artificial intelligence intended for the analysis of mammographic data for the identification or exclusion of the presence of breast cancer is basically a procedure configured to allow the development of an artificial intelligence that provides considerable assistance to a technician specialized in mammographic data processing. Basically, therefore, it trains artificial intelligence to reproces the mammographic data to classify any anomalies found within the data and referring to any breast tumours or to exclude a priori the presence of tumours avoiding, for example, the detection of false positive.

In other words, the training process allows you to instruct the artificial intelligence to identify only the true positives, and/or the true negatives. The true positives are to be identified as the cases in which the presence of tumour lesions is identified, without the errors given by false positives, that is, by the results of tests that lead erroneously to accept the hypothesis on which it was conducted. The true negatives are to be identified as the cases in which the absence of tumour lesions is identified, without the errors given by false negatives, that is, by the results of tests that lead erroneously to reject the hypothesis on which it was conducted.

The process is preferably implemented by a system that is made up of all the apparatuses configured to allow the realization of the different phases of the process as better described later on.

Briefly, the procedure includes at least one acquisition phase of the mammographic data.

The acquisition phase can be carried out by a plurality of different apparatuses. Therefore, such apparatuses can be included within the system.

For example, the acquisition phase can be performed by radiographic or tomographic instruments or, in any case, configured to allow at least one mammographic image of a user to be determined.

Furthermore, the acquisition apparatuses can include simple processors, for example computers, smartphones, tablets or other similar means, configured to allow the editing and exchange of information in textual format or even metadata relating to parts of text or even images.

Advantageously, the apparatuses, and therefore also the process, are configured to allow the acquisition of mammographic data coming from different sources.

The term "source" obviously means a device from which the mammographic data originates, such as, for example, one of the acquisition systems described above. With the expression "mammographic data" it is meant the set of data that define the information regarding the breasts of at least one user.

The mammographic data advantageously include at least three different sources. In particular, they include mammographic images of a user, report texts and reports relating to the user's mammographic images, and structured data in an electronic medical record, also conventionally defined with the acronym EMR, including at least metadata relating to at least part of the same mammography images.

Mammographic images can be of various types: for example, they can include one or more of a choice between a full-field digital mammography (FFDM), a digital breast tomosynthesis (DBT), an ultrasound (US), a computerized axial tomography (TAC) and a magnetic resonance imaging (MRI).

In general, and advantageously, digital mammographic images are complete images, full images, and are not limited only to regions of interest, also commonly known in the sector as RoI (Region of Interest).

The regions of interest are regions of the human body affected by one or more potentially cancerous lesions, i.e. which could correspond to cancer. Therefore, a digital mammography image can include one or more RoIs.

The report texts relating to the user's mammographic images are substantially entirely textual data that are conventionally drawn up by technicians in the sector, i.e.

radiologists, breast specialists or other experts, able to provide a written interpretation of what can be seen from the mammographic images, for example with regard to what appears in the images and also to the detailed characteristics of the subject of the images themselves, for example description of a specific lesion, position of the lesion, dimensions, or more.

Therefore, the reports texts and reports are complete texts, i.e. full text, and are not limited to predefined lexicons, such as BI-RADS, or to a group of predefined and synthetic keywords or terminologies.

Structured data can include, for example, one or more of choice between reports and images retrieved from hospital clinical systems (SIO), electronic medical record (EMR), Breast imaging-reporting and data system (BI-RADS) and Digital Imaging and Communications in Medicine (DICOM). Basically, in general, structured data refers to the set of images and related characteristics, or metadata, referring to the images themselves such as, for example, breast density, shape and margins of the nodules, location and morphology of the lesion, cancer score breast.

Basically, the structured data could in part correspond with the set of mammographic images and report texts organized in a pre-organized structure.

Advantageously, the process comprises a processing step.

In the processing phase, the mammographic data are processed through algorithms implementing a deep neural network, also known by the acronym multimodal DNN. The multimodal DNN is advantageously configured to develop a mammographic data analysis model. This model therefore determines the operating logic of artificial intelligence.

The latter, or the deep neural network, is substantially implementable through an algorithm executed by a computer. Therefore, the system may include a computer configured to execute the deep neural network operating algorithm.

Naturally, moreover, the computer could be operationally connected to one or more servers, even in the cloud. Therefore, the mammographic data could also be recorded inside said servers and determine a source database through which to define a set of training source data including the mammographic data.

In fact, the latter, before being used, are often subject to processing for anonymization in order to respect the privacy, and therefore compliance with the regulations referring to this, of each of the users whose data are analysed.

The servers could substantially determine a pool of anonymous mammographic data from which the computer, and therefore the deep neural network, or artificial intelligence, can draw on for training.

In any case, the analysis model is created by performing a cross-learning, or cross-learning, starting from all the mammographic data and, in more detail, on the basis of the respective sub-phases of analysis.

Preferably, the processing comprises at least the first classification, association and second classification sub-phases.

In the first classification sub-phase, basically, each of the mammographic images is classified through a multi-label classification. In particular, each image is discretized in a plurality of portions.

The portions of images may therefore or may not correspond to regions of interest. This classification is also implemented through a model with an Encoder-Decoder architecture based on a convolutional neural network, also known by the acronym CNN and/or a neural network based on Transformers.

The CNN is a feed-forward artificial neural network that has been successfully implemented in the domain, above all, of the artificial vision. The main strength of a deep CNN lies in the large number of trainable parameters in different layers.

A Transformer is a feed-forward neural network model that implements a mechanism called self-attention, thanks to which it is able to encode and decode input sources effectively. It also exploits a large number of trainable parameters arranged in different layers.

Examples of image classification can be, for example, determined as "Negative", "Positive-benign", "Positive-malignant" and in general in such a way as to be able to correctly label the reference image.

In the association sub-phase, parts of the report texts are preferably associated with one or more portions of images and/or with parts of said structured data.

This last sub-phase is preferably implemented through an Encoder-Decoder type model based on a neural network of the Transformer type and/or a bidirectional long-term memory, known as Bi-LSTM.

In particular, the latter extrapolates from the description found in the text of the report/medical report, the classification characteristics of the images, for example as described above, and metadata, such as description of the lesion, location of the lesion, dimensions or more.

A bi-directional LSTM is a type of DNN that performs well for typical sequence prediction tasks, because it can take context from the previous steps. The Bi-LSTMs increase the amount of contextual information available by also including a forward pass in the network, in the right context of the backward pass sequence of the network itself.

The second classification sub-phase includes the multi-label classification of each of the structured mammography data.

Also in this case, preferably, the classification is implemented by an Encode-Decoder model based on a convolutional neural network, and/or in combination with a Transformer.

The Encode-Decoder type model can perform multi-label classification on any structured data, such as BI-RADS report and DICOM file. Moreover, more in detail, in the second classification sub-phase, characteristics of the images classified in the first classification sub-phase and part of the metadata relating to the classified images can be mutually associated.

In fact, the Encoder-Decoder type model can be configured to extract image classification functions, such as "Negative", "Positive-benign", "positive-malignant", and metadata, such as breast density, shape and margins. of nodules, location and morphology of the lesion, breast cancer score which may already be partly present in the images and in the report text.

The amount of data, especially images, to be analysed at least in the first classification sub-phase can be, in some cases, a limit for the realization of a fully functional analysis model.

Therefore, the process can include a further pre-training phase.

The pre-training phase, if any, is prior to the acquisition phase.

In summary, the pre-training phase is aimed at providing preliminary training to artificial intelligence so that the latter is already prepared to be able to complete its training with a smaller amount of data.

A small amount of data means, for example, a number of mammographic training images, and related report texts and structured data, at least less than 30,000 units. Even more preferably, a number less than 10,000 units is meant.

The pre-training phase therefore includes an execution phase of predetermined generic models of data interpretation with the deep neural network, or DNN, and a phase of refinement of the deep neural network DNN in which the acquisition and processing of a limited amount of specific mammography data are carried out.

Basically, therefore, in the execution phase, artificial intelligence learns to manipulate and interpret mammographic data on the basis of generic models that are already known and easily available.

Such models can include, for example, for report texts and structured data one or more of a choice between a model of the Transformers family such as BERT, RoBERTa, DistillBert but not limited to these, Word2Vec and Elmo word embeddings, and for images at least ImageNet.

Basically, the pre-training phase allows to determine a transfer of learning from a previous generic model to the model developed through the training procedure. Hence, transfer learning enables the transfer of knowledge learned from a non-detailed data set to a specific data set, such as mammography data.

The procedure advantageously also comprises a generation phase and displaying output data.

The generation is substantially determined by the processing of the mammographic data as previously described. So, in fact, the generation is done automatically by the processing and is the result of the classification.

In the visualization phase, possibly carried out by a visualization device operatively connected to the computer which includes the DNN, the output data of the analysis model are displayed starting from mammographic data sets of input.

Such output data preferably comprise:
a representation of at least one region of interest including lesions,
a classification of the lesion,
metadata associated with the corresponding region of interest, and
parts of report texts and reports corresponding to the region of interest.

In particular, preferably, the classification of the lesions present in the region of interest can be detailed in at least three cancer classes, for example negative, positive-benign, positive-malignant with automatic production of statistical confidence criteria for the certainty of the result.

The structured data, produced automatically, can include metadata associated with the region of interest and therefore with the lesion, such as, for example, breast density; presence of nodules/tumour masses with description, size, location and morphology of the lesions, or shape and margins of the nodules; presence of micro-calcifications with morphology and distribution of lesions, or even category position and BI-RADS score.

The parts of the report, also produced automatically, can therefore include other characteristics of any lesions, for validation by the radiologist.

It is important to underline that the identification, and subsequent representation, of the region of interest depends on the processing of mammographic data and is therefore an important output data, automatically generated by the procedure, and not as input or selected by an external operator at the beginning of the procedure.

The invention therefore comprises a new training system for artificial intelligence intended for the analysis of mammographic data for the identification or exclusion of the presence of sense cancer. The new training system is thus able to identify true positives and/or true negatives.

This system substantially implements the process as previously described. Therefore, it may include the process, the servers and the apparatuses configured to allow the process to be carried out.

FIG. 1 shows a drawing of a computer 10 connected to an external hard disk 20 for an embodiment of a data processing system of the invention comprising means for implementing performance of the procedure according to the invention.

Furthermore, the invention includes a new computer program. The computer program, or the algorithm, comprising instructions which, when the program is executed by the computer, allow the computer to carry out the training method according to the invention.

In addition, the invention includes a new storage medium. The storage medium, which can also be part of the server or servers, possibly even virtual and part of a Cloud-type environment, is readable by a computer comprising instructions which, when executed by the computer, allow the computer to perform the procedure according to the invention.

In conclusion, the invention comprises a novel use of mammographic data including mammographic images of a user, report texts relating to the mammographic images of said user, and data structured in an electronic medical record (EMR) including at least metadata relating to at least part of the mammography images, to perform cross-learning of mammography data configured to allow training an artificial intelligence configured to develop a mammography data analysis model.

The training procedure for artificial intelligence intended for the analysis of mammographic data for the identification or exclusion of the presence of breast cancer according to the invention achieves important advantages.

In fact, the procedure and related system allow to create an artificial intelligence able to help the diagnosis work of qualified personnel, for example a radiologist, by providing very accurate mammographic data analysis tools.

Generally, reading and interpreting a mammogram are difficult tasks for radiologists as breast cancer screening has a high rate of false positive recall (i.e., 15%). All the European countries, following the European guidelines for quality assurance in breast cancer screening and diagnosis, have therefore introduced the so-called "double reading" for which a mammogram is read independently by two radiologists. The use of a "second reader" according to the Guidelines reduces the number of screening test errors by 5-15%. However, when using a second reader, a further problem that arises is the agreement among the readers and, therefore, the reader consent rate can in turn vary from 5% to 22% depending on the study setting.

The artificial intelligence trained with the method according to the invention allows to validate what is usually elaborated by experts in the field, if not to avoid double reading by providing a validation system which, on balance, is extremely performing. In particular, artificial intelligence is able to skim the results inferable from mammographic data both in a positive sense, identifying cases relating to true tumour lesions, and in a negative sense, identifying false negatives with excellent certainty, eliminating cases relating to false commonly found injuries. More specifically, artificial intelligence is able to skim the results by defining the true positives and/or true negatives, thus eliminating the true negative cases from the human reading and signalling the true positive cases to the human reading.

Considering the conventional performance indices, also known as KPIs, for evaluating the performance relative to the accuracy of the data processed by the artificial intelligence model, it is possible to obtain performances that are superior to human ones, especially when the artificial intelligence system is used as a second reader and in combination with the radiologist's reading.

The procedure, therefore, allows to create an artificial intelligence that assists radiologists by increasing their performance, reducing trivial activities and streamlining daily workflows.

Furthermore, the knowledge transfer techniques implemented by the pre-training phase make it easy to carry out the training of artificial intelligence, with good performance values, even in the face of limited amounts of data.

The invention is susceptible of variants falling within the scope of the inventive concept defined by the claims.

In this context, all the details can be replaced by equivalent elements and the materials, shapes and dimensions can be any.

The invention claimed is:

1. A training procedure process for artificial intelligence intended for the analysis of mammographic data for the identification or exclusion of the presence of breast cancer, or for the automatic identification of true negative and true positive cases, comprising:
   acquiring a plurality mammographic data from a plurality of different sources and including at least:
   digital mammographic images of a user,
   text of reports and reports relating to said mammographic images of said user, and
   data structured in an electronic medical record (EMR) including at least metadata relating to at least part of said mammographic images,
   processing said mammographic data through algorithms implementing a multimodal deep neural network (DNN) configured to develop an analysis model of said mammographic data by performing cross-learning based on sub-phases of:
      first multi-label classification of each of said mammographic images implemented through a machine learning model with Encoder-Decoder architecture based on a convolutional neural network (CNN) and Transformers,
      association of parts of said report texts with one or more of said portions of images and/or with parts of said structured data implemented through a neural network model with Encoder-Decoder architecture based on a bidirectional long-term memory (Bi-LSTM) and Transformers,
      second multi-label classification of each of said mammographic structured data implemented through a neural network model with Encode-Decoder architecture based on a convolutional neural network (CNN) and Transformers,
   generating, through said processing, and displaying output data,
   wherein
   said digital mammographic images are complete and full images not limited to regions of interest only, or RoI, including one or more potentially cancerous lesions,
   said complete and full images are made of discretized portions wherein at least one of said portions of said images corresponds to a said region of interest,
   said text of reports and reports are complete or not limited to predefined lexicons, to further comprise,
   said output data includes:
      a representation of at least one said portion corresponding to a said region of interest including lesions,
      a classification of said lesion,
      parts of said structured data associated with said region of interest represented, and
      parts of said report texts associated with said region of interest represented.

2. The process according to claim 1, wherein in said second classification sub-phase characteristics of said images classified in said first classification sub-phase and part of said metadata relating to said classified images are mutually associated.

3. The process according to claim 1, comprising a pre-training phase, preceding said acquisition phase, comprises:
   executing predetermined generic models of data interpretation with said deep neural network (DNN),
   refining said deep neural network (DNN) carrying out said acquisition phase and said processing phase with a limited amount of specific mammographic data.

4. The process according to claim 3, in which predetermined generic models include for said report texts and said structured data one or more chosen from a model of the Transformers family such as BERT, ROBERTa, DistillBert, Word2Vec and Elmo word embeddings, and for said images at least ImageNet.

5. The process according to claim 1, in which said mammographic images comprise one or more of a choice between full-field digital mammography (FFDM), digital breast tomosynthesis (DBT), ultrasound (US), computerized axial tomography (CT) and magnetic resonance imaging (MRI).

6. The process according to claim 1, in which said structured data includes one or more chosen from reports and images retrieved from Breast imaging-reporting and data system (BI-RADS) and Digital Imaging and Communications in Medicine (DICOM).

7. A data processing system comprising means for implementing a procedure according to claim 1.

8. A computer program comprising instructions which, when the program is executed by said computer, enable the computer to perform a procedure according to claim 1.

9. The computer readable storage medium comprising instructions which, when executed by said computer, enable said computer to perform a procedure according to claim 1.

10. A method of use of mammographic data including complete and full digital mammography images of a user not limited only to regions of interest including one or more potentially cancerous lesions, complete report texts and reports or not limited to predefined lexicons relating to said mammographic images of said user, and structured data in an electronic medical record (EMR) including at least metadata relating to at least part of said mammographic images, to perform a cross-learning of said mammographic data configured to allow:
   training an artificial intelligence configured to develop an analysis model of said mammographic data according to the training procedure process of claim 1, and
   generating, through said processing, and displaying output data including a representation of at least one said region of interest including lesions, a classification of said lesion, parts of said structured data associated with said represented region of interest, and parts of said reports texts associated with said region of interest represented.

11. The process according to claim 2, comprising a pre-training phase, preceding said acquisition phase, comprises:

executing predetermined generic models of data interpretation with said deep neural network (DNN), refining said deep neural network (DNN) carrying out said acquisition phase and said processing phase with a limited amount of specific mammographic data.

12. The process according to claim 11, in which predetermined generic models include for said report texts and said structured data one or more chosen from a model of the Transformers family such as BERT, ROBERTa, DistillBert, Word2Vec and Elmo word embeddings, and for said images at least ImageNet.

13. The process according to claim 12, in which said mammographic images comprise one or more of a choice between full-field digital mammography (FFDM), digital breast tomosynthesis (DBT), ultrasound (US), computerized axial tomography (CT) and magnetic resonance imaging (MRI).

14. The process according to claim 13, in which said structured data includes one or more chosen from reports and images retrieved from Breast imaging-reporting and data system (BI-RADS) and Digital Imaging and Communications in Medicine (DICOM).

* * * * *